United States Patent [19]

Salahuddin et al.

[11] Patent Number: 5,106,731

[45] Date of Patent: Apr. 21, 1992

[54] KAPOSI'S SARCOMA ENDOTHELIAL CELLS AND GROWTH FACTOR

[75] Inventors: Syed Z. Salahuddin, Gaithesburg; Shuji Nakamura, Rockville; Robert C. Gallo, Bethesda, all of Md.

[73] Assignee: The United States of America as represented by the Department of Health and Human Services, Washington

[21] Appl. No.: 261,014

[22] Filed: Oct. 21, 1988

[51] Int. Cl.$^5$ .................. C12Q 1/02; C07K 15/08; C07K 17/00

[52] U.S. Cl. ...................... 435/7.24; 435/7.23; 435/240.2; 435/804; 530/351; 530/828; 530/300; 530/388.24; 530/389.2

[58] Field of Search ............... 435/240.2, 240.23, 804, 435/7.24, 7.23; 530/351, 387, 828, 300

[56] References Cited

PUBLICATIONS

Delli-Bovi et al. "Processing Secretion and Biological Properties of the Fibroblast Growth Factor..." *Molec. Cell. Biol.* 8(7), 2933-2941 (Jul. 1988).

Pasquale Delli Bovi, Anna Maria Curatola, Francis G. Kern, Angela Greco, Michael Ittmann, and Claudio Basilico; "An Oncogene Isolated By Transfection Of Kaposi's Sarcoma DNA Encodes a Growth Factor That Is A Member of the FGF Family" *Cell*, vol. 50, 729-737 Aug. 28, 1987.

Article by Y. C. Cui, P. C. Tai, K. C. Gatter, D. Y. Mason & C. J. F. Spry; "A vascular endothelial cell antigen with restricted distribution in human foetal, adult and malignant tissues" *Immunology* 1983 49 183-189.

Article by Pasquale Delli-Bovi, Anna Maria Curatola, Karen M. Newman "Processing, Secretion, and Biological Properties of a Novel Growth Factor of the Fibroblast Growth Factor Family with Oncogenic Potential" *Molecular and Cellular Biology*, Jul. 1988, pp. 2933-2941.

Article by Eric A. Jaffe, Leon W. Hoyer, Ralph L. Nachman, entitled "Synthesis of von Willebrand Factor by Cultured Human Endothelial Cells " *Proc. Nat. Acad. Sci.* U.S.A. vol. 71, No. 5, pp. 1906-1909, May 1974.

Article by I. Gery, R. K. Gershon and B. H. Waksman entitled "Potentiation of Cultured Mouse Thymocyte Responses by Factors Released by Peripheral Leucocytes" The *Journal of Immunology* vol. 107, No. 6 pp. 118-1780.

Article by Shuji Nakamura, S. Zaki Salahuddin, Peter Biberfeld, etc. "Kaposi's Sarcoma Cells: Long-Term Culture with Growth Factor From Retrovirus-Infected CD4+-T Cells" *Science*, vol. 242 pp. 426-430.

*Primary Examiner*—Sam Rosen
*Attorney, Agent, or Firm*—Cushman, Darby & Cushman

[57] ABSTRACT

The present invention relates to a growth factor found in HTLV-II conditioned media and to compositions containing same. The growth factor of the present invention supports the growth of Kaposi's sarcoma endothelial-like cells. The factor has a molecular weight of 30K to 35K in monomeric form and a molecular weight of about 70K in dimeric form.

6 Claims, 11 Drawing Sheets

KAPOSI'S SARCOMA ENDOTHELIAL CELLS AND GROWTH FACTOR

A growth factor which supports growth of Kaposi's sarcoma and which contains neoangiogenic properties has been isolated. Tests which utilize this growth factor in growth media have use as tools in diagnosis of Kaposi's sarcoma and in evaluation of the disease process. The assay systems used for monitoring the activity of this growth factor and the resulting growing AIDS-KS cells are valuable tools, since they will facilitate the evaluation of the drugs and therapeutic strategy.

BACKGROUND OF THE INVENTION

Previous to its recognition as an AIDS-associated disease (1), Kaposi's sarcoma (KS), initially described in three fatal cases of sarcoma by Mortiz Kaposi in 1872, was primarily found in elderly men (over 50 years of age) of Eastern European, Mediterranean, or African descent. The clinical, histopathological and epidemiological aspects of the endemic or classical form of KS found in these populations have been studied extensively. In African patients, KS generally presents as either an indolent disease in elderly people or an aggressive infiltrative or nodular disease in young individuals. The latter has many features in common with those observed in patients with HIV-1 infection. Kaposi's sarcoma, with a pattern similar to that found in AIDS patients, also occurs at an increased frequency in transplant recipients and in patients receiving immunosuppressive therapy. Histological observations have shown that KS lesions contain proliferating spindle cells (probably of lymphatic origin), as well as other endothelial cells, fibroblasts, erythrocytes, and infiltrating leukocytes. A very important feature of the KS lesion is the presence of extensive neovascularization.

An unusual feature of KS is its appearance as a multifocal neoplastic lesion. This suggests a polyclonal origin rather than a classical malignancy involving an initial clonal cell transformation followed by metastasis. Despite abundant epidemiological data, the etiology and pathogenesis of KS is still unknown. Genetic factors (such as HLA patterns), viral involvement (such as Epstein-Barr virus and human cytomegalovirus), and chemical effects (such as amyl nitrate usage), acting independently or in concert, have all been suggested as contributing elements. However, none of these factors have been convincingly linked to the cause or pathogenesis of any form of KS. In contrast, there is a clear correlation between HIV-1 infection and the new aggressive form of epidemic KS, while other forms of KS have no HIV-1 association. However, HIV-1 is apparently not directly involved in the origin of this neoplasm by a direct multi-focal transformation of progenitor cells, since HIV-1 nucleotide sequences have not been detected in the DNA of KS tissues. Moreover, the greater incidence of KS in HIV-1-infected homosexual males compared to other groups at risk for AIDS has lead to the suggestion that other environmental factors or possibly another virus (with HIV-1) might be involved in the initiation and/or maintenance of AIDS-KS.

Definitions and Sources of Materials

Growth factors used include: endothelial cell growth supplement (ECGS); basic fibroblast growth factor (bFGF); epidermal growth factor (EGF); platelet derived growth factor (PDGF); interleukin-1 (IL-1); nerve growth factor (NGF)(Collaborative Research, Inc., Lexington, Mass.); tumor necrosis factor alpha (TNFα); interferon gamma (INFγ)(Amgen Biologicals, Thousand Oaks, Calif.); transforming growth factor Beta (TFGβ)(R&D Systems, Inc., St. Louis, Mo.); interleukin-2 (IL-2)(Cellular Products, Inc., Buffalo, N.Y.); interleukin 4 (ICN, Cleveland, Ohio); and granulocyte-monocyte colony stimulating factor (GM-CSF)(Genzyme, Boston, Mass.). Heparin for bioassay (SIGMA, St. Louis, Mo.) and affinity chromatography (Pharmacia, Upsalla, Sweden), were obtained as indicated. These factors were used under the same condition and tested for $^3$H-thymidine uptake and cell number assay. See Example I.

STATEMENT OF DEPOSIT

The cell lines of the invention have been deposited under conditions to assure access to the subject matter to the public during pendency of the application in accord with requirements under 37 CFR 1.14 and 35 U.S.C. 122 in the American Type Culture Collection in Rockville, Md. KSEL-3 was deposited as AIDS-KS 3 On Oct. 21, 1988.

The deposited material will be maintained for at least five (5) years after the most recent request for a sample; for a period of 30 years from the date of deposit; or for the life of the patent, whichever period is longest. If the deposited sample should become contaminated or nonviable, the sample will be replaced.

DESCRIPTION OF FIGURES

NOTE: Many long irregular mitochondria (M), fine microfilaments (F) beneath the cell membrane (FIG. 1B). Gap junction (GJ) and also the pinocytotic vesicle (PV) are shown in FIG. 1C (60,000×).

The inset in the upper left-hand corner of FIG. 1B: KSEL-3 cell showing microvilli. (scanning electron micrograph 1000×)

FIG. 5 Comparison of the conditioned media (CM) from different human T-cell lines for their growth-promoting activity for KS-derived endothelial-like cells (KSEL-1). HTLV-I- and HTLV-II-infected cell lines developed from infected human fetal cord blood leukocytes transformed by HTLV-I, with in vitro and human T-cell lines H9 infected by HIV-1 and HUT 78 infected by HIV-$2_{DZ}$ were used for these experiments. CM was harvested at 4-5-day intervals from infected and uninfected cells cultured at an initial density of $1 \times 10^6$ cells/ml. All supernatant fluids were clarified by both low-speed (2,000 xg) and high-speed centrifugation (45,000 rpm for 1 hr.). These CM were then dialyzed against PBS, passed through 0.45 m Millipore filters, and stored at −20° C. for at least two weeks before use. CM were diluted 1:4 with RPMI 1640 before testing. The cell number of treated cells was determined on the sixth day of culture by trypsinization and quantitation using a Coulter particle counter. The activities of these CM were compared to KSEL-1 growth in ECGS (30 g/ml) plus heparin (45 g/ml) or in standard culture media.

Inset: In vitro cumulative growth of KS-derived cells in culture media supplemented with HTLV-II CM (20% v/v) for over more than 6 passages. The initial seeding density of KS-derived cells was $0.5 \times 10^6$ cells/75 cm² flask.

FIG. 7 Heparin affinity chromatography of HTLV-II CM. Heparin-sepharose (Pharmacia, Uppsala, Sweden) was equilibrated with 0.1M NaCl+0.01M Tris-GHCl (pH=7.0). 4000 units of HTLV-II CM (unit was estimated with effective dose for 50% of maximum growth response of KSEL-1 cells) was applied in 0.1M NaCl+0.01M Tris-HCl buffer and eluted in stepwise manner with 0.5M NaCl (fraction II), 1.2M NaCl (fraction III), 1.5M NaCl (fraction IV) and 3.0M NaCl (fraction V) in addition to 0.01M Tris HCl.

Each fraction was collected, concentrated by ultrafiltration (YM-5, Diaflo) and dialyzed against PBS. These fractions were then assayed for growth stimulation of the KS-derived cells, KSEL-1, (●—●) and normal vascular endothelial cells (o—o) at the indicated dilution. Recovery rate of activity was estimated with half maximum effective dose. Basic FGF from bovine pituitary was used as positive control and identified in fraction IV and V. Total recovery rate was 42% of the applied activity. Sixty-seven percent of the recovered activity in both assays was identified in fraction I and 33% in fraction II.

Description of the Invention

Cell lines have been established from Karposi's sarcoma lesions in tissue culture. The discovery of a new growth factor produced by human retrovirus-infected T4 lymphocytes that can support the long-term growth of these KSEL cell lines (over one year for more than 30 passages) provides important means of diagnosis of Karposi's sarcoma and a method for evaluation of the progress of the disease process.

Figure 5:
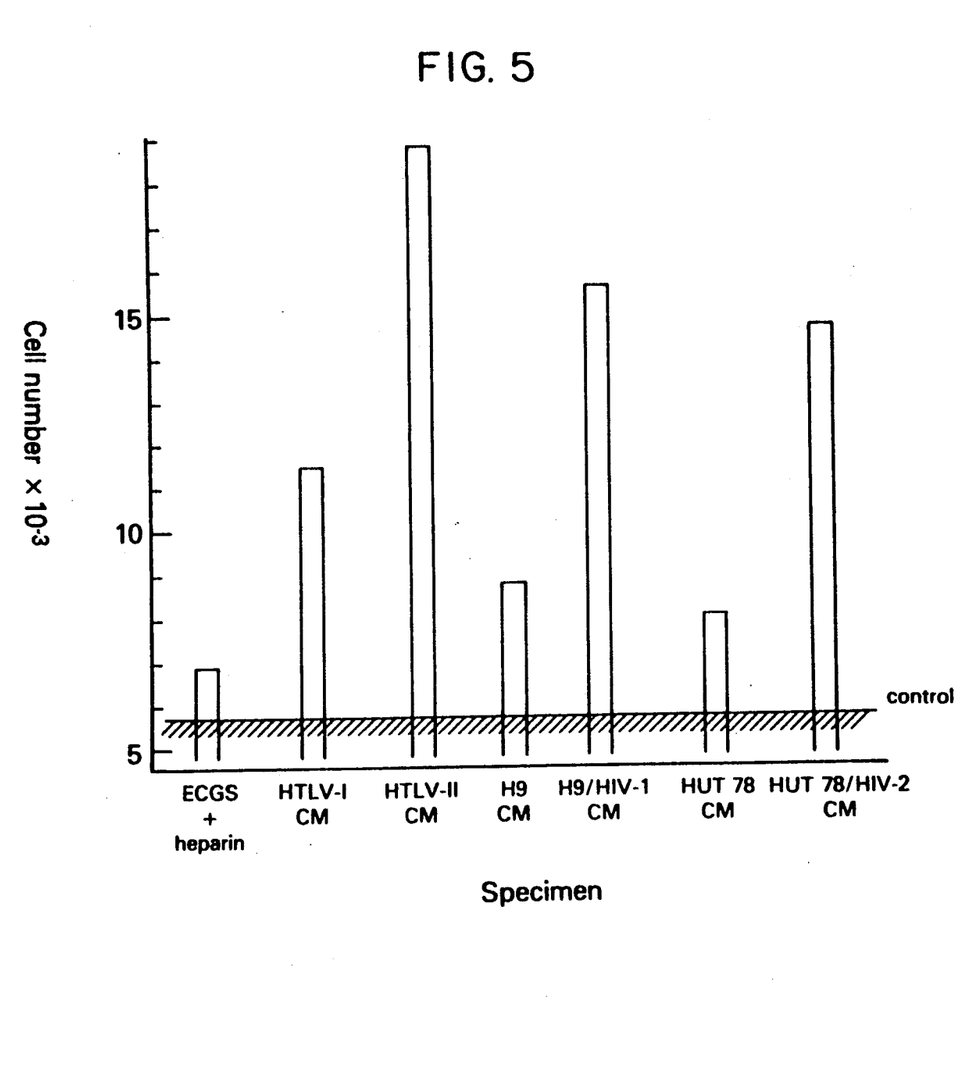

The system developed for the in vitro cultivation of KS-derived cells is dependent upon the induction of growth by a factor present in the conditioned media (CM) of human retrovirus-infected T-4 human lymphocytes, especially HTLV-II transformed cells. The cultured human KS-derived cells can be continuously grown. The cells have properties of endothelial cells but differ from normal vascular endothelial cells in several respects. The growth factors induce neoangiogenesis in the chick chorioallantoic membrane (CAM) assay; and they induce a KS-like lesion in the nude mouse with new blood vessel formation, proliferating fibroblasts, spindle cells, and infiltrating leukocytes. All of the cells of the KS-like lesions were demonstrated to be of mouse origin. Initial attempts to grow the pertinent cells from AIDS-KS lesions using minced biopsy tissues and standard culture techniques yielded only fibroblastic cells. While several available growth factors strongly stimulated DNA synthesis and growth of normal vascular endothelial cells, most had little or no effect on Karposi's sarcoma endothelial-like KSEL) cells. For example, as summarized in Table 3, DNA synthesis of human umbilical vein endothelial cells (H-UVE) was stimulated by ECGS, basic FGF (bFGF), EGF, PDGF, and IL-1, and that of bovine capillary endothelial cells (BCE) by ECGF and bFGF, and slightly by EGF. Fibroblastic cells established in cell culture from a KS lesion (KSF) and normal human foreskin fibroblast(s)(HSF) were also slightly stimulated by ECGS and bFGF. KSEL cells, however, responded weakly and transiently to IL-1 and TNFα. Searching for a more potent KSEL cell growth-promoting activity, we also tested conditioned media from T-cells infected by HTLV-I or HTLV-II or by other human retroviruses, via HIV-1 or HIV-2. As summarized in FIG. 5, conditioned media from several cell lines infected by these viruses supported the growth of KSEL cells (KSEL-1). CM from a HTLV-II non-productively infected, transformed T-cell line, (HTLV-II CM) consistently produced the highest levels of this activity and was selected for further studies.

Figure 6A:
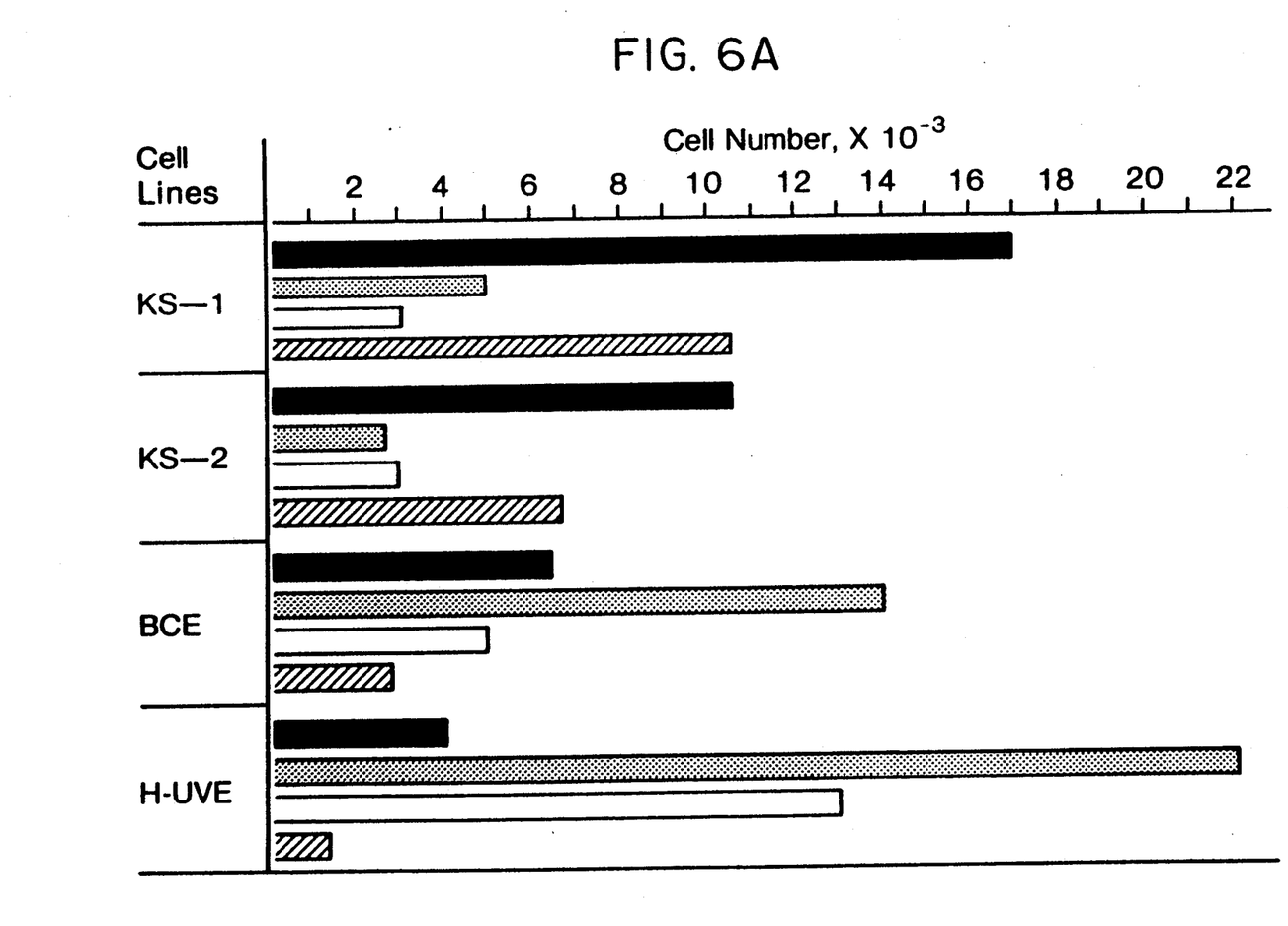
FIG. 6A Comparison of effects of known endothelial and/or fibroblast growth factors, ECGS, bFGF and IL-1 with HTLV-II CM for growth of KSEL cells and normal vascular endothelial cells. For these experiments $3 \times 10^3$ KSEL cells and $5 \times 10^3$ H-UVE or BCE cells were seeded per well. The number of cells used as controls without added factors were: $4.0 \times 10^3$ KSEL-1, $3.6 \times 10^3$ KSEL-2, $2.2 \times 10^3$ BCE, and $1.8 \times 10^3$ H-UVE cells. Cell number was determined o the sixth day in culture following initial seeding of duplicate cultures:
represents 1:8 dilution of HTLV-II CM;
30 g/ml ECGS + 45 g/ml heparin;
50 ng/ml bFGF;
5 u/ml IL-1

The effect of HTLV-II CM on the growth of two cell cultures derived from Kaposi's sarcoma tissues (KSEL) and normal endothelial cells was then compared with several factors reported to have endothelial cell growth promoting activity (FIG. 6A). Consistent with the stimulation of DNA synthesis described in Table 3, ECGS and bFGF supported the growth of normal endothelial but not of KSEL cells. In contrast, HTLV-II CM preferentially did support the growth of KSEL cells and to a lesser extent that of normal endothelial cells. IL-1 and TNF, which stimulated KS and/or normal endothelial cell DNS synthesis (Table 3), also supported the short-term growth of KSEL cells.

Figure 1A:
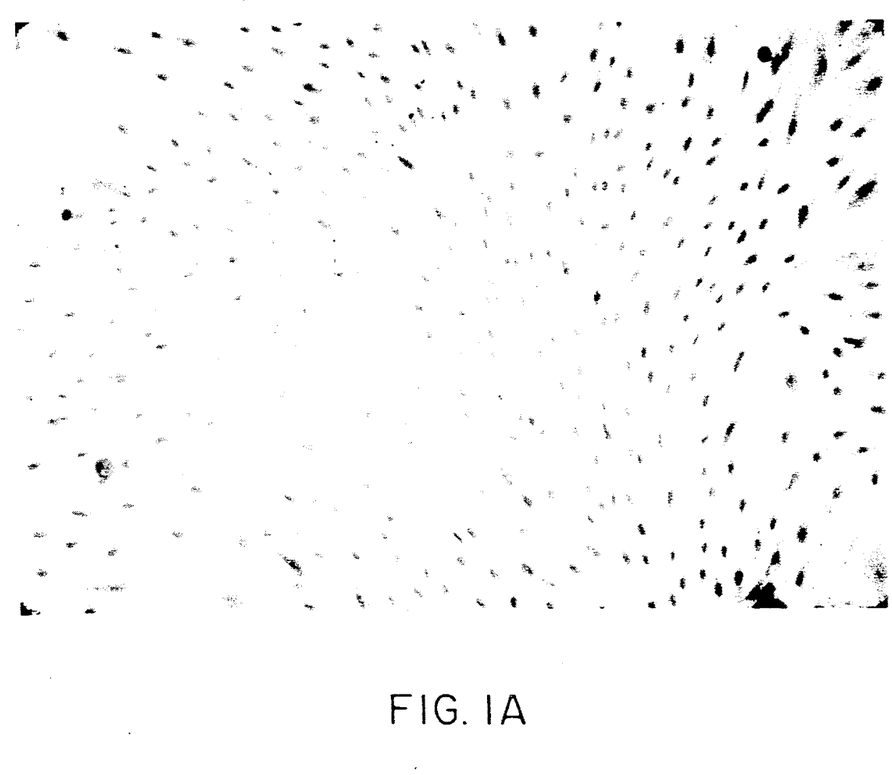
FIG. 1A Long-term cultured confluent KSEL cells stained with Wright-Giemsa showing spindle shaped cells.
Figure 1B:
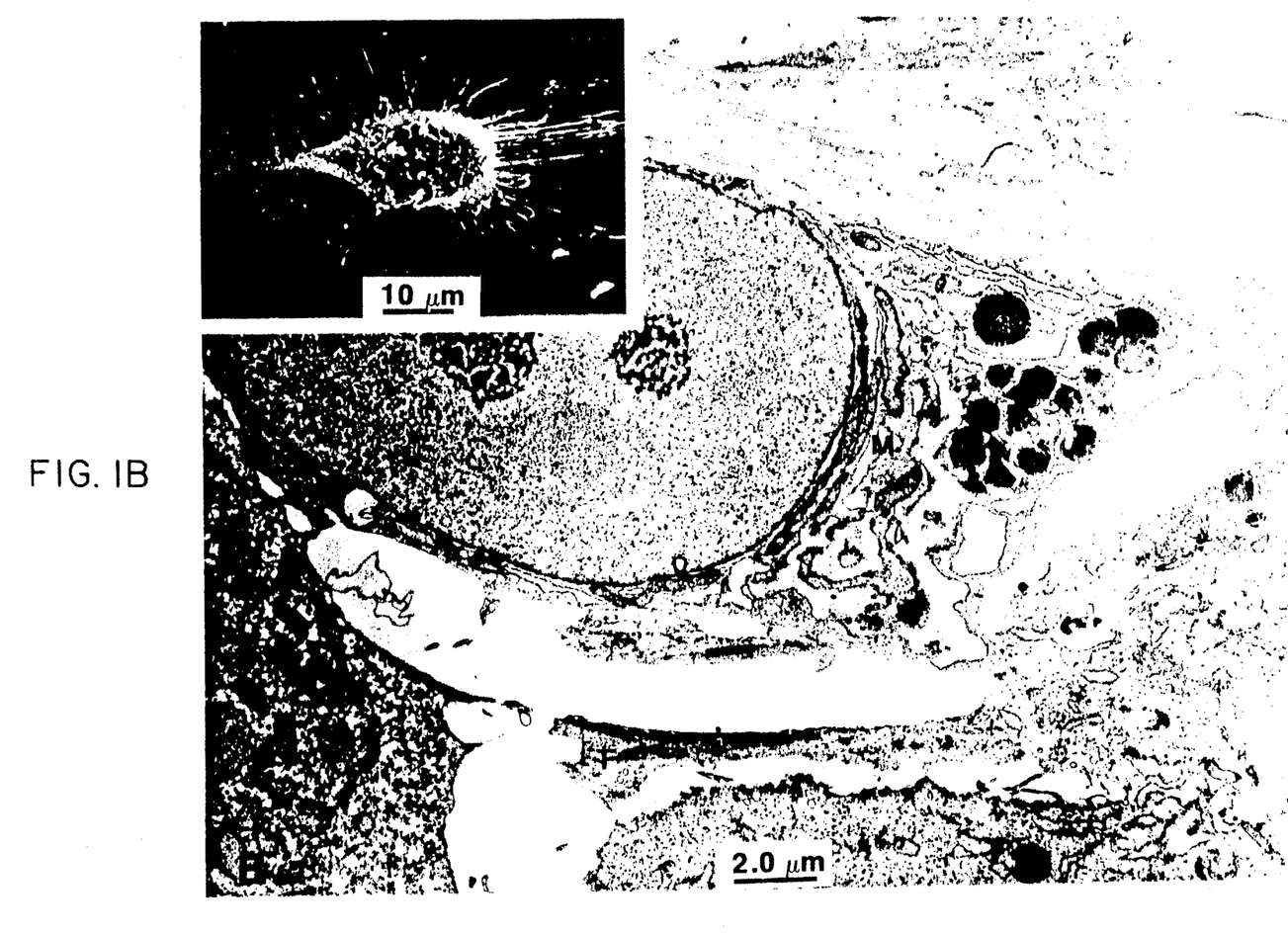
FIG. 1B Electron micrograph of KSEL-3 cells from a confluent cell culture (9,000×). The cells were fixed by addition of 2% glutaraldehyee and subsequently detached from the plastic plates by dissolution of the plastic as previously described.

Presently, long-term KS tissue-derived cell cultures, KSEL-1 through KSEL-6, have been isolated. Cell lines KSEL-2 and -3 were initiated from lung biopsies, and the remainder from pleural effusions from male AIDS-KS patients using procedures described herein. Morphological evaluation of these cultured cells demonstrated several features characteristic of spindle cells described in KS tissues and endothelial cells of lymphatic origin. For example, the KS cells in culture are usually elongated and polymorphic, with a prominent "dendritic" spindle-like appearance (FIG. 1A). Features characteristic for human endothelial cells were also evident at the ultrastructural level. These included microfilament beneath the cell membrane, long convoluted mitochondria and microvilli covering the apical surface (FIG. 1B). Additional features such as tight and gap junctions and pinocytotic vesicles on the apical and basal cell surfaces were also seen (FIG. 1C). The KS cultured cells, however, lacked the Weibel-Palade bodies seen primarily in normal endothelial cells of vascular origin but not observed in some primary KS tissues.

Consistent with a general lack of any specific chromosomal abnormalities reported in cells from KS tissues, analysis of the KS-derived cell lines generally demonstrated a normal human male diploid karyotype (46 XY). The most common variation observed was a missing Y chromosome in some cells which frequently occurs in cultured cells.

It had been suggested that the prominent spindle cell in KS tissues is an endothelial cell, likely of lymphatic origin. To further elucidate the endothelial cell lineage of the KS cell lines which was suggested by their morphological characteristics, histochemical and immunohistochemical studies were performed. Immune histochemical studies were performed using monoclonal antibodies specific for endothelial cells and other cell types. As summarized in Table 1, these tests demonstrated that the factor VIII related antigen (fraction VIII: Ag), described by Jaffe, et al, [*Proc. Nat'l Acad. Sci, USA,* 71, 1906 (1974)], commonly found in endothelial cells of vascular origin, was present in the normal human vascular endothelial cell line (H-UVE) but not in the KS-derived cell lines. Primary KS tissues have also been reported to be negative for the F VIIIR: Ag. Monoclonal antibody EN-4 described by Cui, et al, [*Immunology,* 49, 183 (1983)], which detects a plasma membrane antigen of vascular and lymphatic endothelial cells and KS spindle cells in tissues, did not interact with the KS-derived cells and was at background levels with H-UVE. Another monoclonal antibody, PAL-E, which recognizes an antigen selected with pinocytic vesicles in cells of the vascular but not lymphatic endothelium and KS spindle cells in primary tissue, detected antigen in H-UVE cells only. Both H-UVE and the KS cells reacted with antibody against an inhibitor of plasminogen activator, TPAI, which is secreted by endothelial cells. Antibodies to intermediate filaments, vimentin, cytokeratin, desmin and keratin, and antibodies to fibronectin were also treated. Vimentin, cytokeratin, and fibronectin, which are commonly expressed in mesenchymal cells have been found in both H-UVE and KS cells, whereas neither desmin which is expressed in skeletal, visceral and certain vascular smooth muscle cells, nor keratin, which is expressed in ectodermal cells were found in either.

Histochemical assays for specific enzymatic activities commonly associated with endothelial tissues have also been performed. These results further demonstrated similarities and differences between H-UVE and the KS-derived cells. ATPase and angiotensin converting enzyme (ACE), which are known to be present in vascular but not lymphatic endothelium, were present in H-UVE only, whereas naphthyl acetate esterase, acid phosphatase, and 5' nucleotidase activities were present in both H-UVE and, KSEL cells. Alkaline phosphatase, routinely found in vascular endothelial cell tissue sections, was not found either in H-UVE or KS-derived cells.

Two additional cytochemical markers routinely used to distinguish endothelial cells from other cell types have also been found at high levels in both H-UVE and KS cells.

The pattern of reactivities seen in the KS cells, i.e., negative results for fraction VIII R:Ag, EN-4, PAL-E, ATPase, alkaline phosphatase and ACE and positive results for TPAI, 5' nucleotidase, UEA-1 and Ac-LDL suggest that the KS-derived cells have features of endothelial cells of lymphatic origin, as has been previously suggested for the KS spindle cells. The possible lymphoid tissue origin of the endothelial cells was also supported by the lack of Weibel-Palade bodies. Henceforth, these cultured spindle cells are called KS-endothelial or KSEL cells.

TABLE 1

Characteristics of KS-derived and Normal Human Endothelial Cells

| Assay for Endothelial Cells | H-UVE | KS-derived Cell Lines |
|---|---|---|
| Immunohistochemical Assay[1] | | |
| FVIIIR:Ag | ++ | − |
| HLA Class II | − | − |
| EN-4 | + | − |
| PAL-E | +++ | − |
| TPAI | ++ | +++ |
| Fibronectin, Vimentin, Cytokeratin | + | + |
| Desmin | − | − |
| Keratin | − | − |
| Enzyme Histochemical Assay[2] | | |
| ATPas | ++ | − |
| ACE | ++ | − |
| Acid Phosphatase | + | ++ |
| Alkaline Phosphatase | − | − |
| 5' Nucleotidase | + | + |
| Cytochemical Stains[3] | | |
| UEA-I | +++ | +++ |
| Ac-LDL Uptake | +++ | ++ |

In addition to the characteristic spindle cells, developing KS lesions contain many other cell types including vascular endothelial cells, fibroblasts, erythrocytes and various lymphocytes, the lesions undergo a striking vascularization (neoangiogenesis). Other characteristics of the KS-derived cell lines consistent with their involvement in the development and/or maintenance of the KS lesion were identified. Conditioned media (CM)(also referred to as Karposi's sarcoma growth factor), from several of these KS cell lines have been analyzed for the biological activities supporting and affecting cell growth, cell mobility or invasive properties.

Figure 2A:
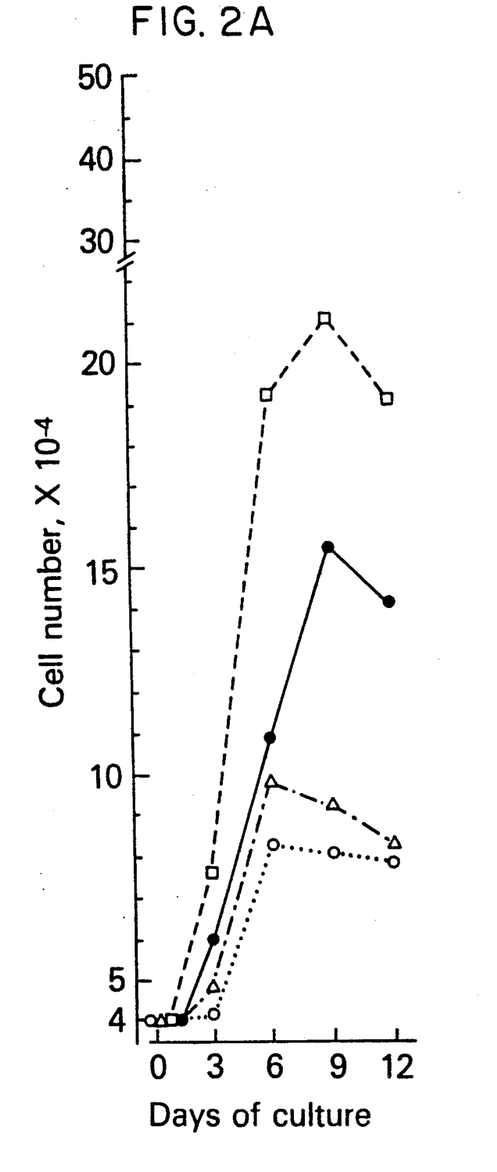
FIG. 2 Growth kinetics of KSEL (Panel A) and H-UVE cells (Panel B) showing differences-in their responses to in vitro culture conditions: (0...0) routine medium, RPMI 1640 supplemented with 15% fetal calf serum; (Δ—.—Δ), endothelial cell growth supplement (ECGS), plus heparin, (⊖—⊖) conditioned media (CM) from HTLV-II infected T4 cells (20% v/v); extract of KSEL cells (O.D.$_{280}$=0.05); and (■—■) CM from KSEL cells alone (25% v/v)(Panel B). Initial seeding density 4×10$^4$ in each case.
Figure 2B:
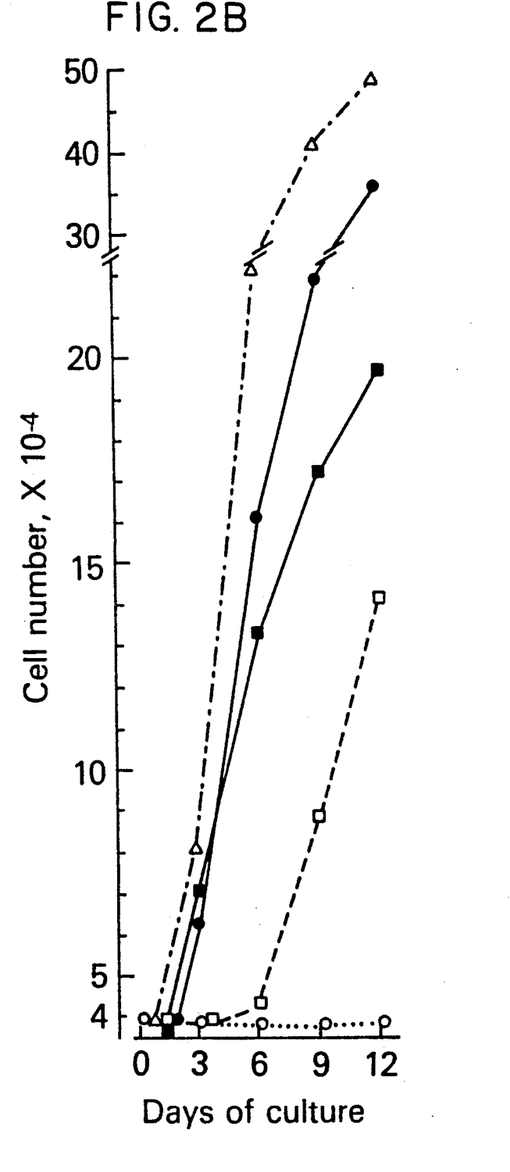
Figure 3:
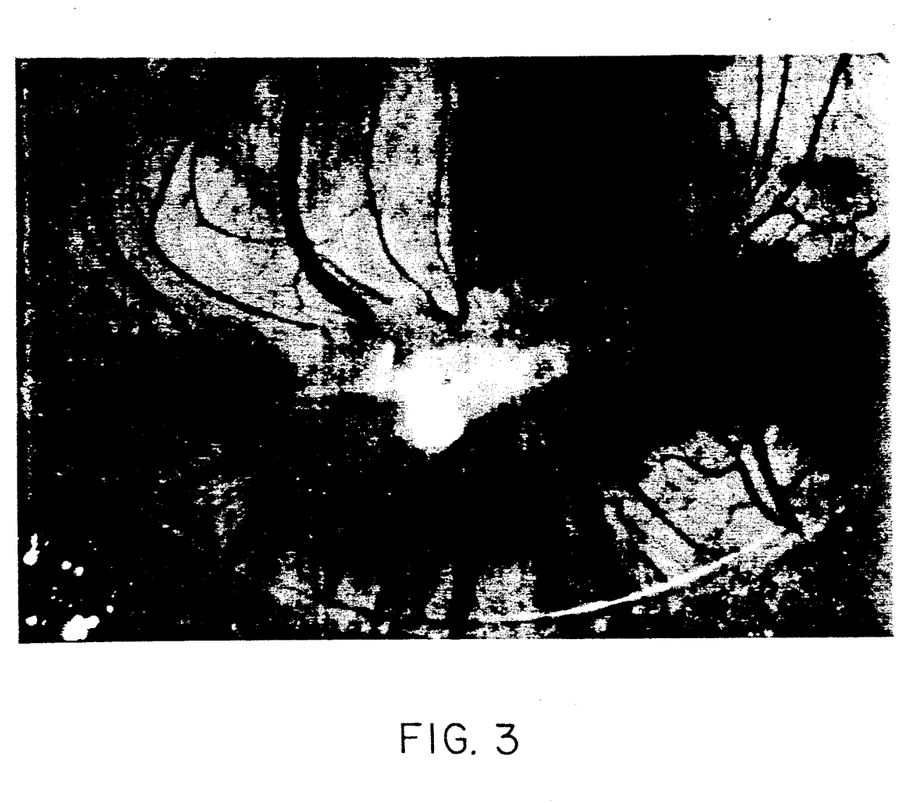
FIGS. 3 Induction of neoangiogenic response in a 12-day fertilized chicken chorioallantoic membrane (CAM)(24) by 2×10$^4$ KSEL cells. NOTE: numerous formed small vessels in the CAM in the Panel.

An example of the growth of H-UVE and the KSEL cells in response to their own CM, CM from HTLV-II infected cells and ECGS is shown in FIG. 2. HTLV-II CM supports growth of both KS and normal endothelial cells. Interestingly, CM from KSEL cells (KSEL CM) also contained an activity able to stimulate and support their own growth, that of other KSEL cells, and also H-UVE cells. These same activities were found at much greater concentrations in extracts of these same cells. Because it had been found earlier that interleukin-1 (IL-1) had a slight but significant growth-promoting effect on KS-derived endothelial cells, the cell lines were examined for the presence and release of IL-1 using the thymocyte co-mitogenic assay of Gery, et al [J. Immunol. 107, 1778 (1971)]. IL-1 like activity was detected in supernatant fluids and in extracts of the KS cells. The synthesis of mRNA for IL-1, several other growth factors, and cell regulatory activities by the KS cell lines were further shown by molecular analysis of specific mRNA.

Figure 6B:
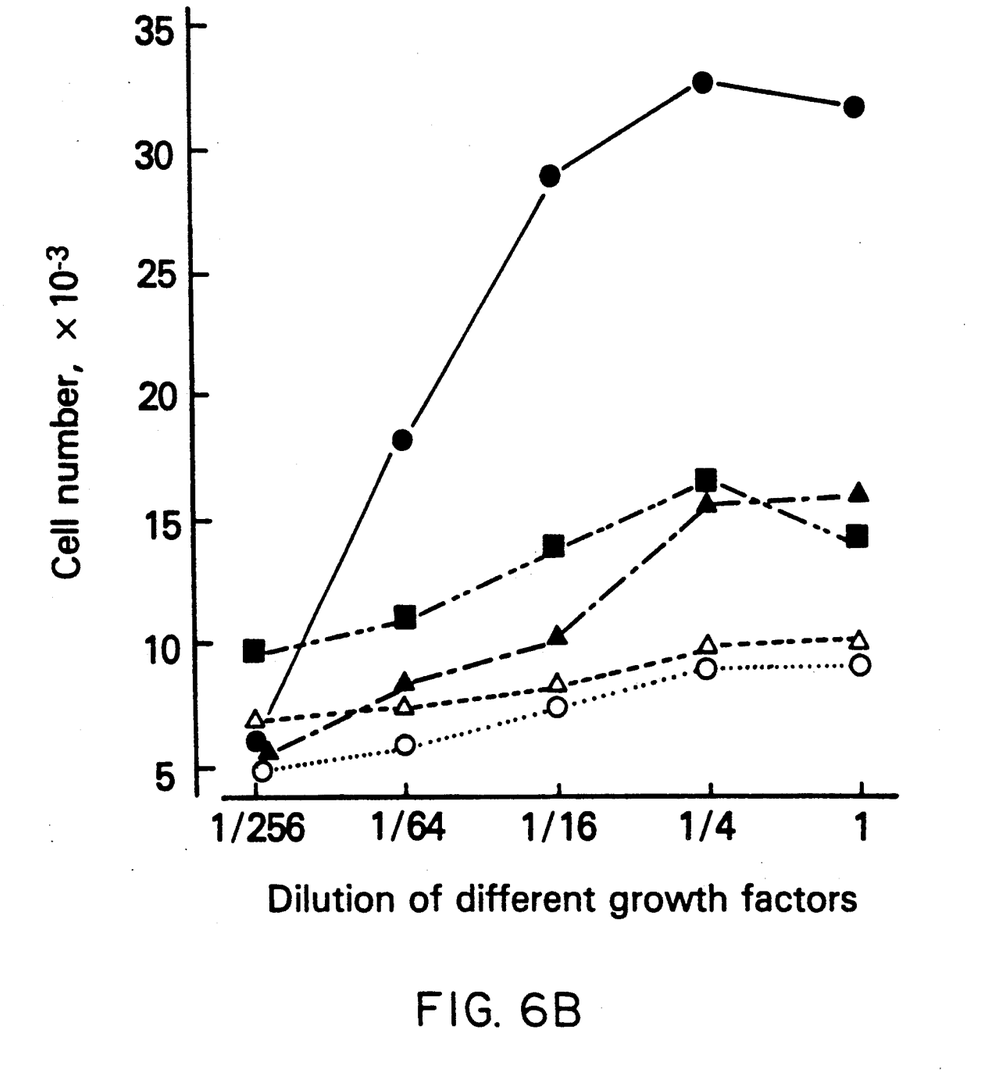
FIG. 6B Short-term growth of KSEL cells to various concentrations of known cytokines and HTLV-II CM. Serum-free HTLV-II CM or different cytokines were serially diluted and added to the KS-derived cell culture KSEL-1. The growth of the KSEL-1 cells was monitored as described in the FIGS. 1 and 2A. Assays were initiated with the same number of cells ($3 \times 10^3$) and cell number was determined on day six of culture.
o—o represents HTLV-II CM;
▲ --- ▲ (5 u/ml);
■ --- ■ TNF (20 u/ml);
△ --- △-0 IFN (100 u/ml);
o . . . o bFGF (50 ng/ml)
Figure 7:
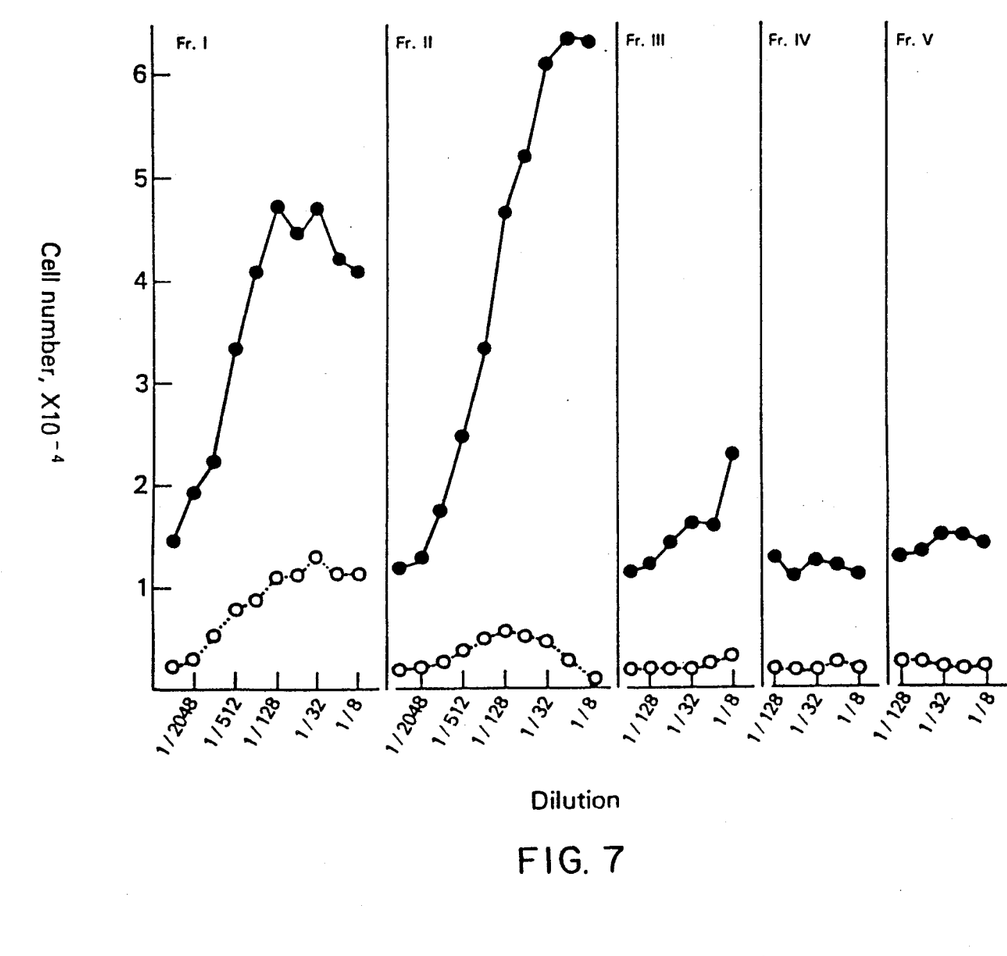

An example of effect of HTLV-II CM on KSEL-1 cells is shown in FIG. 6B. As indicated, HTLV-II CM strongly supported the growth of KSEL-1 cells in a dose dependent manner, whereas the levels of maximum activity with IL-1 and TNF were significantly lower at the highest concentrations tested. Also as expected, no significant activity was found using bFGF and interferon gamma (INF )(FIG. 6B). Furthermore, under optimum conditions, the KSEL cells, supported by HTLV-II CM, can be grown in cell culture for prolonged periods of time. An example of the growth kinetics of KS-derived cells, KSEL-1, and H-UVE cells grown in the presence of comparable concentrations of HTLV-II CM is shown in FIG. 7. Using these conditions, the KSEL cells could be grown indefinitely with an average doubling time of 30 to 43 hours (over one year to date) while normal endothelial cells, e.g., H-UVE cells can be propagated for less than two months. By contrast, IL-1 and TNFα under optimum conditions supported KSEL cell growth for less than six passages. As indicated by the cumulative number of KSEL-1 cells shown in the inset for FIG. 7 use of HTLV-II CM gives us an opportunity to accumulate KSLE cells for detailed characterization. Biological observations, therefore, clearly demonstrated the presence of activities produced by human retroviral-infected cells able to stimulate and support the growth of both normal and KSEL cells.

Figure 8A:
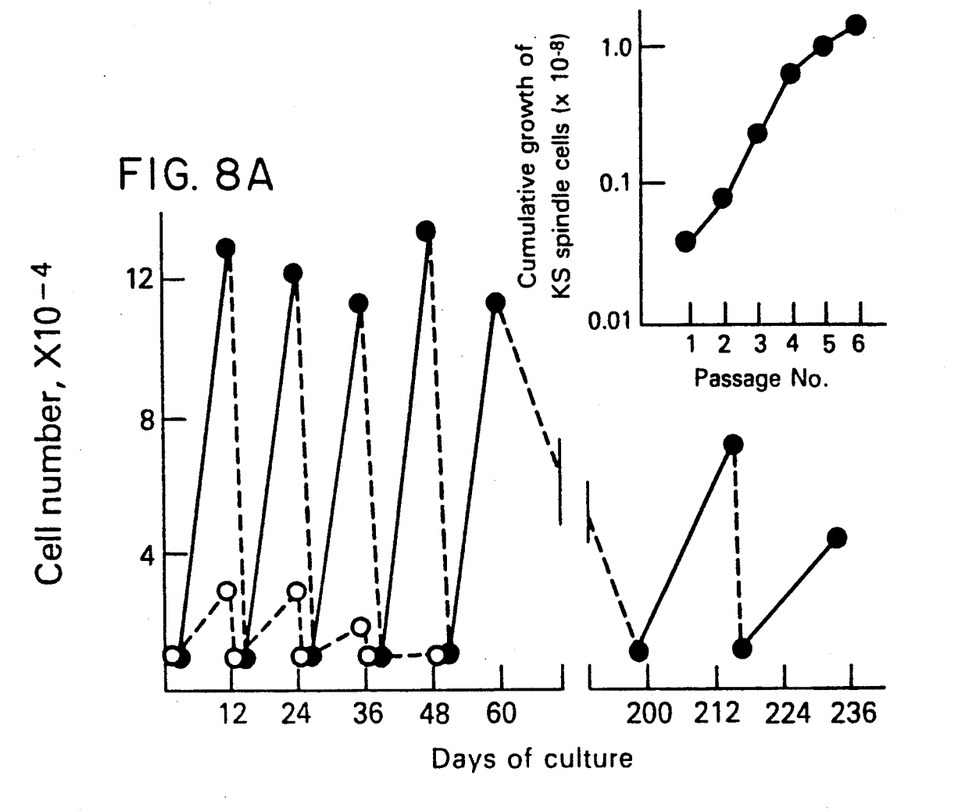
FIG. 8 Growth kinetics of KS-derived cells, KSEL-1 (A), and normal early passage vascular endothelial cells, H-UVE (B), in the presence (●—●) or absence (o—o) of HTLV-II CM (20% v/v). KSEL-1 cells were subcultured continuously, while H-UVE cells showed a decreasing response following passage under the same culture conditions.
Figure 8B:
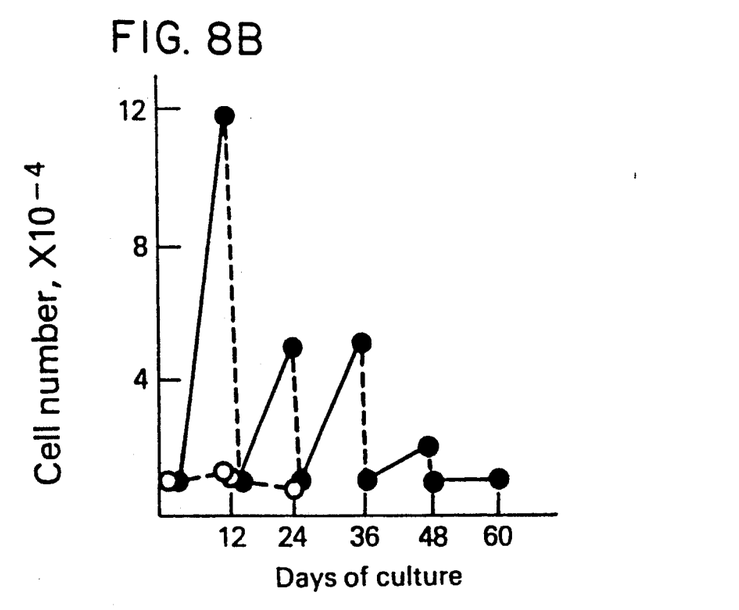

In addition to differences between HTLV-II CM and other factors in their ability to support the long-term growth of KSEL cells, several biochemical characteristics indicated that the active factor in HTLV-II CM has the novel properties of this growth factor. For example, Northern blot analysis of total and poly A-selected RNA from three HTLV-II-infected cell lines demonstrated the possible presence of mRNA for some, e.g., IL-1α, TNFα, TNFβ, IFNγ, GM-CSF, and TGFB but not others, e.g., αFGF, bFGF, IL-1β, IL-2, BCGF, or TGFα factors. Notably absent were mRNA for several normal endothelial cell factors, e.g., a and EGF (closely related to TGFα). Fractionation of HTLV-II CM on a Heparin-Sepharose column and distinguished both KSEL cell and normal endothelial cell growth supporting activities in HTLV-II CM from Heparin-binding factors such as a and bFGF. As shown in FIG. 8, the major HTLV-II CM activities supporting KSEL-1 and normal endothelial cells were identified in the flow through Fraction I and in the low salt eluate Fraction II, indicating little or no Heparin binding. A potent factor for normal endothelial cell growth, bFGF, in contrast, eluted in fraction IV and V. Isoelectrofocus analysis of the activities found in HTLV-II-CM, demonstrated that the factor supporting the growth of KSEL cells had a peak isoelectric point (pI) of 7.3. This value also distinguishes this factor from several other factors, i.e., TNFα, TNFβ, and IL-1α with acidic pI<6.0 factor (Table 2). Other biochemical properties of KSEL cell growth factor compared to some well-known factors are also summarized in Table 2. For example, KSEL cell growth activity in HTLV-II CM was stable while heating for 30 minutes at 37° C. or 60° C., but was eliminated at 100° C. for 3 minutes. This activity was eliminated by treatment with pronase at pH 7.0 and 37° C. for 1 hour. Unlike some other factors, e.g., TNFβ and IL-1α, the KSEL cell growth activity was also sensitive to treatment with trypsin. The KSEL cell growth factor in HTLV-II-CM was also clearly distinguishable from several other factors by molecular size. By Sephadex G-75 gel filtration, the molecular weight of the activity supporting KSEL cell growth was 70K and that for normal endothelial cells was 25K. IL-1, by contrast, was 17K. Further treatment of the 70K fraction chromatography produced a fraction having a molecular weight of 30-35K. The growth factor is shown, therefore to exist as a dimer having a molecular weight of about 70K and a monomer of molecular weight 30-35K.

An evaluation of all biological and biochemical characteristics are consistent with the theory that cells infected by some human retroviruses, e.g., HTLV-I, -II, HIV-1, HIV-2 produce two distinguishable activities, i.e., one with activity for normal endothelial cells and a second factor with activity predominantly for the KSEL cells. The observations indicate clearly that KSEL and normal vascular endothelial cells have distinct growth requirements. Hence, KSEL cells may be distinguished from normal epithelial cells by growth in media to which the novel growth factor taught herein has been added. The use of growth factor can, therefore, be used in differential diagnosis of Karposi's sarcoma.

TABLE 2

Comparison of Biochemical and Biological Characteristics Among KSEL Cell Growth Factor in HTLV-II CM and Other Cytokines Which Can Stimulate the Growth of KSEL Cells

| Characteristics | Factors | | | |
|---|---|---|---|---|
| | TNF | TNF | IL-1 | KSEL Cell Growth Factor |
| Molecular Size | 17K Multimer Dimer On | 20K Multimer Trimer On | 17K | 70K on Gel Filtration Column |
| Isoelectric Point | <5.4 | 5.8 | 5.0 | 7.3 |
| Trypsin Sensitivity | Sensitive | Resistant | Resistant | Sensitive |
| Heat Stability | Relatively Stable (@ 56° C.) | Labile (@ 56° C.) | Relatively Stable (@ 56° C.) | Relatively Stable (@ 60° C.) |
| Lectin Binding Capability | No Bind To ConA Column (Not Glycosylated) | Bind To Lentil Lectin Column (Glycosylated) | No Bind | |
| KSEL Cell Growth Promoting Activity | Weak | | Weak | Strong |
| Fibroblast Growth | Weak | Weak | Weak | Negative |
| Normal Vascular Endothelial Cell Growth | Negative | Negative | Negative | Negative |

TABLE 3

Stimulatin of DNA Synthesis of KSEL Cells and Normal Endothelial Cells by Known Growth Factors

| Growth Factors | Heparin (45 g/ml) | Target Cells Stimulation Index | | | | | |
|---|---|---|---|---|---|---|---|
| | | KSEL-1 | KSEL-2 | BCE | H-UVE | HSF | KSF |
| ECGS | − | 1.3 | 1.1 | 5.7 | 20.8 | 1.3 | 1.9 |
| | + | 1.3 | 1.1 | 9.8 | 45.3 | 1.7 | 2.3 |
| bFGF | − | 0.7 | 0.9 | 6.3 | 40.0 | 1.2 | 2.0 |
| | + | 0.5 | 0.6 | 4.8 | 32.4 | 1.0 | 1.7 |
| EGF | − | 0.5 | 0.9 | 1.6 | 19.0 | 1.2 | 1.5 |
| | + | 0.5 | 0.6 | 1.2 | 14.9 | 1.1 | 1.4 |
| PDGF | − | 0.6 | 1.2 | 1.0 | 10.2 | 1.1 | 1.2 |
| | + | 0.7 | 0.9 | 0.7 | 8.6 | 1.0 | 1.0 |
| IL-1 | − | 2.8 | 2.4 | 1.2 | 12.3 | 0.7 | 1.8 |
| | + | 2.0 | 2.0 | 1.3 | 6.8 | 0.5 | 1.1 |
| TNF | − | 3.2 | 2.6 | ND | 1.5 | ND | ND |
| | + | 2.1 | 2.0 | ND | 1.2 | ND | ND |

Definitions and Discussion of Tables:

KSEL-1 and -2=Spindle-like cells from KS lesions, BCE=Normal bovine capillary endothelial cell, H-UVE=Normal human umbilical vein endothelial cell, HSF=Normal human skin fibroblast, and KSF=Fibroblast from a KS lesion, were tested for their response to well characterized growth factors. ECGS, bFGF, EGF, PDGF, IL-1, and TNF were used.

Numbers indicate the level of DNA synthesis ($^3$H-tdR uptake) used to assess growth factor activity (14). ND=Not Done In addition to factors shown (concentrations tested shown inparenthesis), IL-2 (0.1%–10% volume/volume), TGF, GM-CSF and Heparin did not stimulate the DNA synthesis in either KS-derived or normal vascular endothelial cells.

PDGF and IL-1 on H-UVE cells affected only DNA synthesis did not induce cell growth (data not shown).

Since an accumulation of a number of cell types is characteristic of KS lesion formation, CM from KSEL cells, H-UVE cells, human skin fibroblasts (HSK) and KS-derived fibroblasts (KSF) were also tested for the ability to induce and/or support cell migration and invasion of tissues. The KSEL cells were shown to be substantially more invasive than normal fibroblasts or endothelial cells in response to commonly used attractants, e.g., CM from fibroblastic cells. Furthermore, KSEL cells produce a potent chemotactic activity on smooth muscle, normal endothelial cells, and for other KSEL cells. The KSEL CM also induced these cells to become more invasive.

Other properties of the KSEL cells were found by in vivo experiments. When the KSEL cells were inoculated into the chorioallantoic membrane of 9-day old fertilized chicken eggs, extensive neovascularization characteristic of developing KS lesions was induced and blood vessel development rapidly occurred (Table 4). A much weaker neoangiogenic response was also obtained using cell-free conditioned media (CM) from actively replicating KSEL cells. No activity was detected when cells were fixed before inoculation.

Figure 4A:
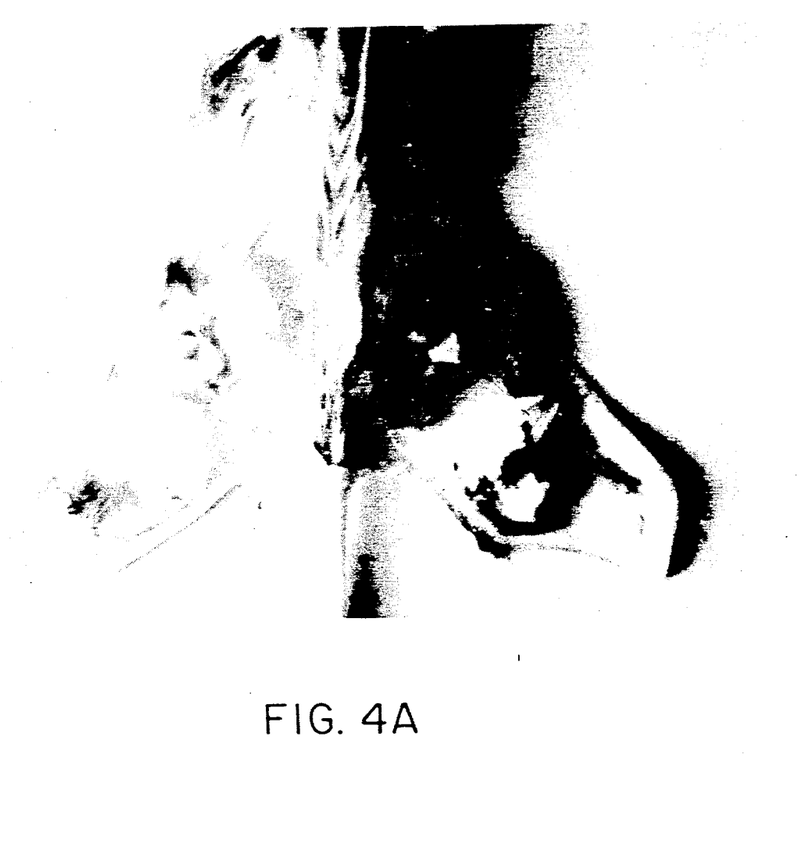
FIG. 4A NCr-nude mice were injected subcutaneously in the lower back with KSEL cells (4×10$^6$ live or fixed cells/site). L=KSEL cells fixed with 0.00125% glutaraldehyde showing a negative reaction. R=Metabolically active KSEL cells giving strong neoangiogenic response.
Figure 4B:
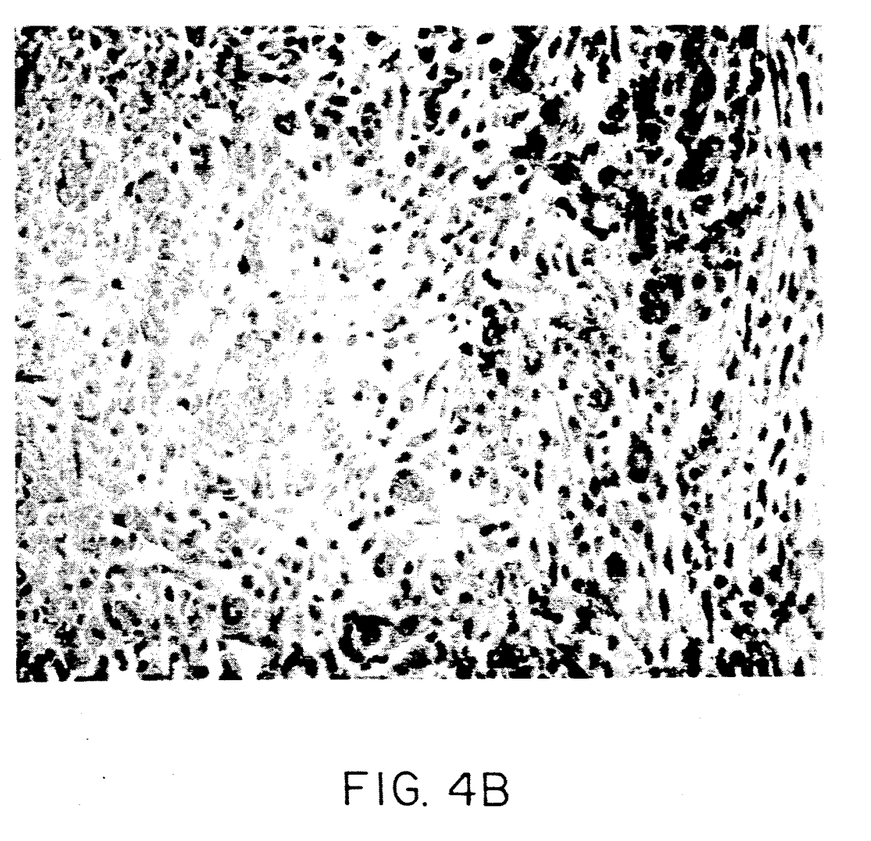
FIG. 4B Histological analysis of the lesion in NCr-nude mouse subcutaneously injected with KSEL cells. Marked response was noted after 4-6 days as illustrated in this hematoxylin eosin stained section. These lesions regressed over a period of two weeks. The responding lesion was comprised of murine cells as evidenced by karyotype analysis. Note the presence of numerous characteristic small vessels (arrows), extravasation (*), and spindle-like cells in the stroma (arrow heads). These are features similar to a human KS lesion (Mag. 800×).

In vivo tests of the KSEL cells for neoangiogenic activity and for induction of KS-like lesions were extended to studies for four strains of nude mice (Beige, Balb/c, Swiss and NCr). When nude mice were inoculated subcutaneously with $4 \times 10^6$ KSEL cells, a highly vascularized new growth developed (FIG. 4A) with mononuclear cell infiltration, and hemorrhage (FIG. 4B). All strains of nude mice tested responded, but the NCr strain showed the most extensive lesion development which occurred 4 to 14 days after inoculation of the cells. These lesions could be restimulated with a fresh inculum of KSE cells.

EXAMPLE 1

Cell line KSEL-1 was established from cells isolated from pleural fluid and KSEL-2 from cells obtained from lung biopsy specimens of AIDS-KS patients. These cells were subcloned and maintained in the gelatinized plastic ware with HTLV-II CM 20% volume/volume (v/v) in addition to RPMI 1640 supplemented with 15% fetal calf serum, containing low lipopolysaccharide (GIBCO, Chagrin Falls, Ohio), 1% Nutridoma (Boehringer-Mannheim, Indianapolis, Ind., 46250), 1% sodium pyruvate (ABI, Silver Spring, MD), 100 g/ml of streptomycin, 100 u/ml of penicillin and 2 mM glutamine. Culture medium was replaced at 3-4 day intervals. After growth to confluence, cells were trypsinized and transferred uniformly at passage ratio of 1:3 for KSEL-1 cells and 1:2 for KSEL-2 cells. Human umbilical vein endothelial cells (H-UVE) and bovine capillary endothelial cells (BCE) were also cultured in the gelatinized flasks with endothelial cell growth supplement 30 g/ml+Heparin (45 g/ml) in addition to base medium. Every 2 days, medium was renewed. After growth to confluence, cells were trypsinized and transferred uniformly at passage ratio 1:5 for H-UVE cells using these conditions H-UVE been maintained and 1:2 for BCE cells for over 1 year, 35 passages, and BCE for 6 months, 15 passages.

TABLE 4

In Vivo Tests for Neoangiogenic Activity of KS and Other Cells in the Chicken Chorioallantoic Membrane (CAM) Assay and in NCr-Nude Mice

| Specimen For Assay | No. Positive/ No. Tested on CAM and (% Positivity) | No. Positive/ No. Tested in Nude Mouse (% Positive) |
|---|---|---|
| KSEL-1 | 13/16 (81) | 3/3 (100) |
| fixed cells | 0/9 (0) | 0/3 (0) |
| KSEL-2 | 10/12 (83) | 9/9 (100) |
| fixed cells | 0/8 (0) | 0/6 (0) |
| KSEL-3 | 7/10 (70) | 8/10 (80) |
| fixed cells | 0/14 (0) | 0/3 (0) |
| KSEL-4 | 6/8 (75) | 3/3 (100) |
| fixed cells | 2/9 (22) | 0/3 (0) |
| KSEL-5 | 12/12 (100) | 2/2 (100) |
| fixed cells | ND | ND |
| KSEL-6 | 12/12 (100) | 2/2 (100) |
| fixed cells | ND | ND |
| KSF | 1/5 (20) | 2/2 (100) |
| SK-HEP-1 | 1/10 (10) | 0/4 (0) |
| MS180 | 6/10 (60) | 0/4 (0) |

Description of Table 4:
KSEL-1 to KSEL-6 are KS endothelial cell clones grown for over a year in culture.
KSF = KS-derived fibroblast
BAE = Bovine aortic endothelial cells
HT-29 = Human colon adenocarcinoma cells
SK-HEP-1 = Human hepatoma cells, producer of bFGF
MS180 = Mouse sarcoma cells
H-UVE, BAE and HT-29 did not show neoangiogenic activity.
ND = Not Done

EXAMPLE 2

Stimulation of DNA synthesis and cell number were measured as follows: $3 \times 10^3$ cells/well Kaposi's sarcoma cells, or $5 \times 10^3$ cells/well normal vascular endothelial (H-UVE and BCE) cells were incubated with 15% FCS ion RPMI 1640 medium in 24 well plate in the absence or presence of test factors or CM. Plating efficiency was approximately 70% for each KS cell culture and 50% for H-UVE and BCE Cells.

EXAMPLE 3

Human umbilical vein endothelial cell (H-UVE) and cell lines established from Karposi's sarcoma tissues (KSEL-1-6) were compared for the primary antigen, enzymatic reactivity, commonly found in some endothelial cells. The reactivity to EN-4 was noted to be very weak with high background and also not specific for endothelial cells.

EXAMPLE 4

Enzyme Histochemical Assays. ATPase. Cells were fixed in 2% paraformaldehyde 5 minutes at room temperature and washed briefly in tap water, immersed in freshly prepared reagents mixture [25 mg adenosine triphosphate (ATP)(Sigma, St. Louis, Mo.), 20 ml of distilled water, 20 ml of 0.2 M Tris-HCl buffer (pH=7.2)m 3 ml of 2% lead nitrate, and 5 ml of 0.25% magnesium sulphate] at 37° C. for 30 minutes. Cells were washed with distilled water, incubated in 5% sodium sulphate solution for 2 minutes, washed in distilled water before observation.

EXAMPLE 5

Alkaline Phosphatase. Cells were fixed with formalin-methanol (1:9) at 4C for 30 seconds, rinsed with distilled water and incubated in freshly prepared reagent mixture, naphthyl-AS phosphate (Sigma) dissolved in 0.5 ml N, N dimethylformamide (DMF)(Sigma), 100 ml of 0.24 Tris-HCl (pH=9.1) and 40 mg Fast TR red (Sigma) were dissolved and filtered at room temperature for 15-20 minutes. After incubation, cells were rinsed 4-5 times with distilled water.

All cells were positive with 2 other cytochemical markers 5' nucleotidase and naphthyl acetate esterase.

EXAMPLE 6

Nucleotidase. Cells were fixed in formalin vapor 5 minutes and rinsed with distilled water. They were incubated with reagents mixture 20 mg adenosine monophosphate (Sigma), 17.6 ml of distilled water, 16 ml of 0.2 M Tris-HCl buffer (pH=7.2), 2.4 ml of 2% lead nitrate (Sigma), and 4 ml of 0.1M Magnesium sulphate (Sigma) were adjusted to pH=7.2 and filtered before use for 30 minutes at 37° C. Cells were rinsed with distilled water, dipped in 2% sodium sulphide and rinsed with tap water.

EXAMPLE 7

Naphytl Acetate Esterase. Cells were fixed for 30 seconds in citrate-acetone-formaldehyde solution (25 ml citrate solution, 65 ml acetone and 8 ml of 37% formaldehyde). Reagent mixture was prepared as follows: 1 ml sodium nitrate solution (Sigma), and 1 ml of Fast blue BB base solution (Sigma) were mixed vigorously with Vortex for 30 seconds and allowed to stand 2 minutes. 40 ml of prewarmed distilled water, 5 ml of Trizmal TM (pH=7.6) buffer concentrate (Sigma) and 1 ml of naphytl acetate solution (Sigma) were added to the above solution. Cells were incubated with a complete set of reagent mixture for 30 minutes at 37° C. with protection of light exposure. After 30 minutes incubation cells were rinsed in distilled water.

EXAMPLE 8

Angiotensin Converting Enzyme (ACE) Assay. $^3$H benzoyl-phe-ala-pro was used as a substrate (Ventrex Laboratories, Inc., Portland, Me., 04103), according to Ventrex manual. By extraction with Ventrex Scintillation cocktail #2, unreacted substrate was separated from $^3$H-benzoyl-phe in organic phase was counted in scintillation counter. The activity of all cell lines was also tested by the addition of specific inhibitor for ACE, SQ 20,881 (Peninsula Laboratories, Belmont, Calif., 94002). 90-95% of this activity was inhibited with $5 \times 10^{-6}$M of this inhibitor.

EXAMPLE 9

Immune Histochemical Assays. Monoclonal antibodies: anti-FVIIIR:Ag (Cappel, West Chester, Pa., 19380) and (DAKOPATTS, Santa Barbara, Calif., 93103); monoclonal anti-tissue plasminogen activator inhibitor (TPA I) antibodies, MC-1, -2, and -3 (kindly provided by Dr. B. Blomback, Karolinska Institute, Sweden); EN-4 and PAL-E (Sambio bv, 5400 Am. Uden, Holland); anti-fibronectin (Hybritech, San Diego, Calif., 92121); anti-vimentin, anti-desmin and anti-cytokeratin (Boehringer Mannheim, Indianapolis, Ind.) and anti-keratin (AE1 and NAE-3; Hybritech) were diluted in PBS or 0.05M Tris-HCl (pH=7.6) before use. Rabbit anti-mouse immunoglobulin (DAKOPATTS) was used as second antibody at 1:20 dilution. Then, 1:20 diluted APAAP-mouse (DAKOPATTS) was inclubated at 37° C. for 60 minutes. Fast red (Vector Laboratories, Inc., Burlington, Calif., 94010) was used as substrate.

EXAMPLE 10

Cytochemical Stain, Ulex Europaeus-I Agglutimin (UEA-1). FITC-conjugated UEA-I (Vector Laboratories, Inc.) was incubated with acetone-fixed cells at 37° C. for 1 hour. To check the specificity of UEA-I, lectin was preincubated with 0.2M L-fructose (Sigma), at room temperature for 30 minutes and no binding result was observed. Acetylated Low Density Lipoprotein (Ac-LDL) Uptake. 1, 1'-dioctadecyl-1-1,3,3', 3'-tetramethyl-indo-carbocyamine perchlorate (Dil-Ac-LDL)(Biomedical Technologies, Inc., Cambridge, Mass., 02141) was used as probes. 10 ug/ml of Dil-Ac-LDL was incubated with live cells on the slides, at 37° C. for 4 hours. The cells were washed with probe-free media 4-5 times and kept in media for observation. Uptake was visualized under fluorescence microscope with standard rhodamine excitation:emission filters.

— = negative
+ = weak positive
+ + = moderate positive
+ + + = strong positive

See Table 4.

The growth factor and antibody to the factor may be used in the diagnositic assays to confirm diagnosis of Karposi's sarcoma. Suspensions of cells obtained by biopsy of lesions in patients may be grown in cell culture in the manner disclosed herein or by any equivalent method known in the art. (See Example 1.) Comparison of growth patterns of KSEL cell lines of the present invention, non-KS cell lines such as H-UVE and BCE, and test cells from biopsy in media containing one of several known growth factors, including HTLV-II CM indicated cells obtained from KS lesions show the response patterns of the KSEL cell lines. Both the dimer having a molecular size of about 70 kD and the monomer having a molecular size of 30 kD to 35 kD support growth of cells of KS origin.

Monoclonal and polyclonal antibodies may be produced by injection of the growth factor into animals such as mice or rabbits, and purified in accord with known methods. The antibodies so produced may be used as diagnositic tools for detection of the HTLV-II CM growth factor in serum of patients suspected of suffering from Karposi's sarcoma.

We claim:

1. A purified growth factor which supports growth of Kaposi's sarcoma endothelial-like cells (KSEL) having a molecular weight of 30 K to 35 K in the monomeric form or about 70 K in the dimeric form.

2. A composition of matter comprising a growth factor of claim 1 in a carrier.

3. A composition of matter comprising a growth factor of claim 1 in a growth media.

4. A composition of claim 2 wherein the growth factor exists primarily as a dimer.

5. A kit for diagnosing Kaposi's sarcoma comprising a composition of claim 3 and a Kaposi's sarcoma endothelial cell line.

6. A composition of matter comprising a growth media and a cell line which is KSEL 3.

* * * * *